(12) United States Patent
Liu et al.

(10) Patent No.: US 9,326,710 B1
(45) Date of Patent: May 3, 2016

(54) CONTACT LENSES HAVING SENSORS WITH ADJUSTABLE SENSITIVITY

(71) Applicant: Verily Life Sciences LLC, Mountain View, CA (US)

(72) Inventors: Zenghe Liu, Alameda, CA (US); Brian Otis, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 671 days.

(21) Appl. No.: 13/623,155

(22) Filed: Sep. 20, 2012

(51) Int. Cl.
| | |
|---|---|
| *A61B 5/02* | (2006.01) |
| *A61B 5/145* | (2006.01) |
| *A61B 5/00* | (2006.01) |
| *A61B 3/10* | (2006.01) |
| *H05K 3/46* | (2006.01) |
| *A61B 5/1473* | (2006.01) |
| *H05K 1/18* | (2006.01) |
| *H05K 3/04* | (2006.01) |

(52) U.S. Cl.
CPC ............... *A61B 5/14532* (2013.01); *A61B 3/10* (2013.01); *A61B 3/101* (2013.01); *A61B 5/1473* (2013.01); *A61B 5/14546* (2013.01); *A61B 5/6813* (2013.01); *A61B 5/6821* (2013.01); *H05K 3/4682* (2013.01); *H05K 1/186* (2013.01); *H05K 3/048* (2013.01)

(58) Field of Classification Search
CPC .................. A61B 5/14532; A61B 5/14865
See application file for complete search history.

(56) References Cited

U.S. PATENT DOCUMENTS

| | | | |
|---|---|---|---|
| 3,958,560 | A | 5/1976 | March |
| 4,014,321 | A | 3/1977 | March |
| 4,055,378 | A | 10/1977 | Feneberg et al. |

(Continued)

FOREIGN PATENT DOCUMENTS

| | | |
|---|---|---|
| EP | 0369942 | 5/1990 |
| EP | 0686372 | 12/1995 |

(Continued)

OTHER PUBLICATIONS

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

(Continued)

*Primary Examiner* — Etsub Berhanu
*Assistant Examiner* — Tiffany Weston
(74) *Attorney, Agent, or Firm* — McDonnell Boehnen Hulbert & Berghoff LLP

(57) ABSTRACT

Apparatus and methods employing contact lenses having electrochemical sensors that have adjustable analyte-sensing sensitivity are provided. In some aspects, level of the analyte or biological substance is detected and a number of sub-electrodes of the sensor are turned on or off based on the level of the analyte or biological substance. The sensitivity of the sensor is adjusted based on the number of sub-electrodes that are turned on or off. In some aspects, the current level from the sensor is employed in determining the number of sub-electrodes to turn on or off. In one aspect, a contact lens includes: a substrate; a power component; a circuit and an adjustment circuit. The circuit can include a potentiostat; and a sensor electrically coupled to the potentiostat, and configured to sense a level of an analyte. The sensitivity of the sensor can be adjustable by the adjustment circuit.

13 Claims, 10 Drawing Sheets

(56) References Cited

U.S. PATENT DOCUMENTS

| | | |
|---|---|---|
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint |
| 5,177,165 A | 1/1993 | Valint et al. |
| 5,177,168 A | 1/1993 | Baron |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 8,608,310 B2 | 12/2013 | Otis et al. |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0192488 A1* | 9/2005 | Bryenton et al. ............ 600/301 |
| 2005/0221276 A1 | 10/2005 | Rozakis et al. |
| 2006/0004272 A1* | 1/2006 | Shah et al. .................. 600/365 |
| 2007/0016074 A1* | 1/2007 | Abreu ........................ 600/475 |
| 2007/0030443 A1 | 2/2007 | Chapoy et al. |
| 2007/0121065 A1 | 5/2007 | Cox et al. |
| 2007/0188710 A1 | 8/2007 | Hetling et al. |
| 2008/0208335 A1 | 8/2008 | Blum et al. |
| 2008/0217173 A1 | 9/2008 | Varney et al. |
| 2008/0218696 A1 | 9/2008 | Mir |
| 2009/0033863 A1 | 2/2009 | Blum et al. |
| 2009/0036761 A1 | 2/2009 | Abreu |
| 2009/0057164 A1 | 3/2009 | Minick et al. |
| 2009/0076367 A1 | 3/2009 | Sit et al. |
| 2009/0118604 A1 | 5/2009 | Phan et al. |
| 2009/0189830 A1 | 7/2009 | Deering et al. |
| 2009/0196460 A1 | 8/2009 | Jakobs et al. |
| 2010/0001926 A1 | 1/2010 | Amirparviz et al. |
| 2010/0013114 A1 | 1/2010 | Bowers et al. |
| 2010/0016704 A1 | 1/2010 | Naber et al. |
| 2010/0028559 A1 | 2/2010 | Yan et al. |
| 2010/0072643 A1 | 3/2010 | Pugh et al. |
| 2010/0109175 A1 | 5/2010 | Pugh et al. |
| 2010/0110372 A1 | 5/2010 | Pugh et al. |
| 2010/0113901 A1 | 5/2010 | Zhang et al. |
| 2010/0133510 A1 | 6/2010 | Kim et al. |
| 2010/0249548 A1 | 9/2010 | Muller |
| 2011/0015512 A1 | 1/2011 | Pan et al. |
| 2011/0028807 A1 | 2/2011 | Abreu |
| 2011/0040161 A1 | 2/2011 | Abreu |
| 2011/0055317 A1 | 3/2011 | Vonog et al. |
| 2011/0063568 A1 | 3/2011 | Meng et al. |
| 2011/0084834 A1 | 4/2011 | Sabeta |
| 2011/0116035 A1 | 5/2011 | Fritsch et al. |
| 2011/0157541 A1 | 6/2011 | Peyman |
| 2011/0157544 A1 | 6/2011 | Pugh et al. |
| 2011/0184271 A1 | 7/2011 | Veciana et al. |
| 2011/0274680 A1 | 11/2011 | Mazed et al. |
| 2011/0286064 A1 | 11/2011 | Burles et al. |
| 2011/0298794 A1 | 12/2011 | Freedman |
| 2012/0026458 A1 | 2/2012 | Qiu et al. |
| 2012/0038881 A1 | 2/2012 | Amirparviz et al. |
| 2012/0041287 A1 | 2/2012 | Goodall et al. |
| 2012/0041552 A1 | 2/2012 | Chuck et al. |

(56) References Cited

U.S. PATENT DOCUMENTS

| | | | |
|---|---|---|---|
| 2012/0069254 A1 | 3/2012 | Burton | |
| 2012/0075168 A1 | 3/2012 | Osterhout et al. | |
| 2012/0075574 A1 | 3/2012 | Pugh et al. | |
| 2012/0078071 A1 | 3/2012 | Bohm et al. | |
| 2012/0088258 A1 | 4/2012 | Bishop et al. | |
| 2012/0092612 A1 | 4/2012 | Binder | |
| 2012/0109296 A1 | 5/2012 | Fan | |
| 2012/0177576 A1 | 7/2012 | Hu | |
| 2012/0201755 A1 | 8/2012 | Rozakis et al. | |
| 2012/0245444 A1* | 9/2012 | Otis et al. | 600/345 |
| 2012/0259188 A1 | 10/2012 | Besling | |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| WO | 95/04609 | 2/1995 |
| WO | 01/16641 | 3/2001 |
| WO | 01/34312 | 5/2001 |
| WO | 03/065876 | 8/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012/052765 | 4/2012 |

OTHER PUBLICATIONS

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Bionic contact lens 'to project emails before eyes,' http://www.kurzweilai.net/forums/topic/bionic-contact-lens-to-project-emails-before-eyes, Last accessed Mar. 14, 2012, 2 pages.
Tweedie, et al., "Contact creep compliance of viscoelastic materials via nanoindentation," J. Mater. Res., Jun. 2006, vol. 21, No. 2, pp. 1576-1589, Materials Research Society.
Brahim, et al., "Polypyrrole-hydrogel composites for the construction of clinically important biosensors," 2002, Biosensors & Bioelectronics, vol. 17, pp. 53-59.
Huang, et al., "Wrinkling of Ultrathin Polymer Films," Mater. Res. Soc. Symp. Proc., 2006, vol. 924, 6 pages, Materials Research Society.
Zarbin, et al., "Nanotechnology in ophthalmology," Can J Ophthalmol, 2010, vol. 45, No. 5, pp. 457-476.
Selner, et al., "Novel Contact Lens Electrode Array for Multi-electrode Electroretinography (meERG)," IEEE, 2011, 2 pages.
Liao, et al., "A 3-µW CMOS Glucose Sensor for Wireless Contact-Lens Tear Glucose Monitoring," IEEE Journal of Solid-State Circuits, Jan. 2012, vol. 47, No. 1, pp. 335-344.
Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.
Thomas, et al., "Functional Contact Lenses for Remote Health Monitoring in Developing Countries," IEEE Global Humanitarian Technology Conference, 2011, pp. 212-217, IEEE Computer Society.

Pandey, et al., "A Fully Integrated RF-Powered Contact Lens With a Single Element Display," IEEE Transactions on Biomedical Circuits and Systems, Dec. 2010, vol. 4, No. 6, pages.
Lingley, et al., "Multipurpose integrated active contact lenses," SPIE, 2009, 2 pages.
Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.
Liao, et al., "A 3µW Wirelessly Powered CMOS Glucose Sensor for an Active Contact Lens," 2011 IEEE International Solid-State Circuits Conference, Session 2, Feb. 21, 2011, 3 pages.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Lončar, et al., "Design and Fabrication of Silicon Photonic Crystal Optical Waveguides," Journal of Lightwave Technology, Oct. 2000, vol. 18, No. 10, pp. 1402-1411.
Baxter, "Capacitive Sensors," 2000, 17 pages.
Lingley, et al., "A Single-Pixel Wireless Contact Lens Display," Journal of Micromechanics and Microengineering, 2011, 9 pages.
"Polyvinylidene fluoride," Wikipedia, http://en.wikipedia.org/wiki/Polyyinylidene_fluoride, Last accessed Mar. 30, 2012, 4 pages.
Murdan, "Electro-responsive drug delivery from hydrogels," Journal of Controlled Release, 2003, vol. 92, pp. 1-17.
Haders, "New Controlled Release Technologies Broaden Opportunities for Ophthalmic Therapies," Drug Delivery Technology, Jul./Aug. 2009, vol. 8, No. 7, pp. 48-53.
Singh, et al., "Novel Approaches in Formulation and Drug Delivery using Contact Lenses," Journal of Basic and Clinical Pharmacy, May 2011, vol. 2, Issue 2, pp. 87-101.
"Contact Lenses: Look Into My Eyes," The Economist, Jun. 2, 2011, http://www.economist.com/node/18750624/print, Last accessed Mar. 13, 2012, 8 pages.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.
Unpublished U.S. Appl. No. 13/240,994, Titled "See-Through Display With Infrared Eye-Tracker," filed Sep. 22, 2011, 38 pages.
Unpublished U.S. Appl. No. 13/209,706, Titled "Optical Display System and Method with Gaze Tracking," filed Aug. 15, 2011, 30 pages.
Adler, "What types of statistical analysis do scientists use most often?" O'Reilly Community, Jan. 15, 2010, 2 pages, http://broadcast.oreilly.com/2010/01/what-types-of-statistical-anal.html, Last accessed Sep. 4, 2012.
Bull, "Different Types of Statistical Analysis," Article Click, Feb. 4, 2008, 4 pages, http://www.articleclick.com/Article/Different-Types-Of-Statistical-Analysis/968252, Last accessed Sep. 4, 2012.
"Understanding pH measurement," Sensorland, 8 pages, http://www.sensorland.com/HowPage037.html, Last accessed Sep. 6, 2012.
"Regression analysis," Wikipedia, 11 pages, http://en.wikipedia.org/wiki/Regression_analysis, Last accessed Sep. 6, 2012.
"Statistics," Wikipedia, 10 pages, http://en.wikipedia.org/wiki/Statistics, Last accessed Sep. 6, 2012.
"Nonlinear regression," Wikipedia, 4 pages, http://en.wikipedia.org/wiki/Nonlinear_regression, Last accessed Sep. 10, 2012.
"Linear regression," Wikipedia, 15 pages, http://en.wikipedia.org/wiki/Linear_regression, Last accessed Sep. 10, 2012.
"Integrated circuit," Wikipedia, 9 pages, http://en.wikipedia.org/wiki/Integrated_circuit, Last accessed Sep. 10, 2012.
"Photolithography," Wikipedia, 8 pages, http://en.wikipedia.org/wiki/Photolithography, Last accessed Sep. 10, 2012.
Harding, et al., "Alcohol Toxicology for Prosecutors: Targeting Hardcore Impaired Drivers," American Prosecutors Research Institute, Jul. 2003, 40 pages.
Kim, et al., "Oral Alcohol Administration Disturbs Tear Film and Ocular Surface," American Academy of Ophthalmology, 2012, 7 pages.

(56) References Cited

OTHER PUBLICATIONS

Quick, "Color-changing electrochromic lens technology has fashion and military applications," Gizmag, Jul. 12, 2011, http://www.gizmag.com/electrochromic-lens-technology/19191/, Last accessed Apr. 12, 2012, 4 pages.

Chu, "Contact Lenses that Respond to Light," Technology Review, Nov. 10, 2009, http://www.technologyreview.com/printer_friendly_article.aspx?id=23922, Last accessed Apr. 12, 2012, 2 pages.

Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.

Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.

Chu et al., "Biomedical soft contact-lens sensor for in situ ocular biomonitoring of tear contents," Biomed Microdevices, 2011, pp. 603-611, vol. 13.

Chu et al., "Soft contact lens biosensor for in situ monitoring of tear glucose as non-invasive blood sugar assessment," Talanta, 2011, pp. 960-965, vol. 83.

Ho et al., "Contact Lens With Integrated Inorganic Semiconductor Devices," MEMS 2008. IEEE 21st International Conference on. IEEE, 2008., pp. 403-406.

Lähdesmäki et al., "Possibilities for Continuous Glucose Monitoring by a Functional Contact Lens," IEEE Instrumentation & Measurement Magazine, Jun. 2010, pp. 14-17.

Lingley et al., "A contact lens with integrated micro solar cells," Microsyst Technol, 2012, pp. 453-458, vol. 18.

Parviz, Babak A., "For Your Eyes Only," IEEE Spectrum, Sep. 2009, pp. 36-41.

Saeedi, E. et al., "Self-assembled crystalline semiconductor optoelectronics on glass and plastic," J. Micromech. Microeng., 2008, pp. 1-7, vol. 18.

Saeedi et al., "Self-Assembled Inorganic Micro-Display on Plastic," Micro Electro Mechanical Systems, 2007. MEMS. IEEE 20th International Conference on. IEEE, 2007., pp. 755-758.

Sensimed Triggerfish, Sensimed Brochure, 2010, 10 pages.

Shih, Yi-Chun et al., "An Inductorless DC-DC Converter for Energy Harvesting With a 1.2-μW Bandgap-Referenced Output Controller," IEEE Transactions on Circuits and Systems-II: Express Briefs, Dec. 2011, pp. 832-836, vol. 58, No. 12.

Shum et al., "Functional modular contact lens," Proc. of SPIE, 2009, pp. 73970K-1 to 73970K-8, vol. 7397.

Stauth et al., "Self-assembled single-crystal silicon circuits on plastic," PNAS, Sep. 19, 2006, pp. 13922-13927, vol. 103, No. 38.

Yao, H. et al., "A contact lens with integrated telecommunication circuit and sensors for wireless and continuous tear glucose monitoring," J. Micromech. Microeng., 2012, pp. 1-10, vol. 22.

Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.

Yao et al., "A contact lens with embedded sensor for monitoring tear glucose level," Biosensors and Bioelectronics, 2011, pp. 3290-3296, vol. 26.

Yao, H. et al., "A Soft Hydrogel Contact Lens with an Encapsulated Sensor for Tear Glucose Monitoring," Micro Electro Mechanical Systems (MEMS), 2012 IEEE 25th International Conference on. IEEE, 2012, pp. 769-772.

Yeager et al., "A 9 μA, Addressable Gen2 Sensor Tag for Biosignal Acquistion," IEEE Journal of Solid-State Circuits, Oct. 2010, pp. 2198-2209, vol. 45, No. 10.

Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

"Alcohol Detection Techonologies. Present and Future," American Beverage Institute, 2009, 9 pages.

Liu et al., "Miniature Amperometric Self-Powered Continuous Glucose Sensor with Linear Response," Analytical Chemistry, 2012, pp. 3403-3409, vol. 84.

\* cited by examiner

CONTACT LENSES HAVING SENSORS WITH ADJUSTABLE SENSITIVITY

TECHNICAL FIELD

This disclosure generally relates to contact lenses having sensors with adjustable sensitivity.

DETAILED DESCRIPTION

Figure 1:
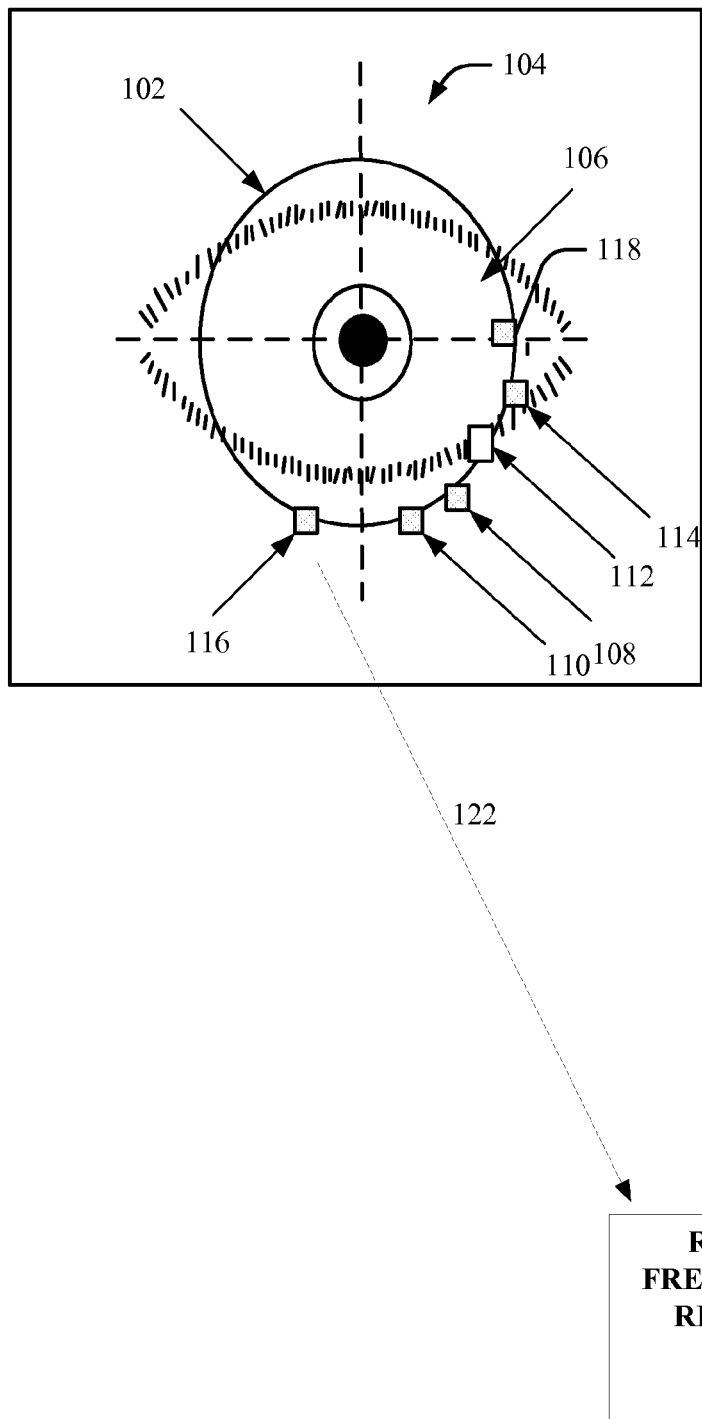
FIG. 1 is an illustration of a block diagram of an exemplary non-limiting system that facilitates contact lenses having sensors with adjustable sensitivity in accordance with aspects described herein.

Various aspects are now described with reference to the drawings, wherein like reference numerals are used to refer to like elements throughout. In the following description, for purposes of explanation, numerous specific details are set forth in order to provide a more thorough understanding of one or more aspects. It is evident, however, that such aspects can be practiced without these specific details. In other instances, structures and devices are shown in block diagram form in order to facilitate describing one or more aspects.

Amperometry is the use of electric current or change in electric current to detect analytes in a solution. Amperometry is typically performed using amperometric electrochemical sensors with electrodes placed in close proximity to a substance being analyzed. Measurements from an electrode are based on an oxidizing or reducing reaction that occurs when the electrode is in proximity to the substance. Proper potentials applied to the electrodes cause such oxidizing or reducing reactions to occur. Resulting electrical currents can be employed in identifying the analyte in some embodiments.

Amperometric sensors often require additional biosensing elements on a working electrode in order for the current-generating redox reaction to occur. One type of biosensing element is oxidase enzyme that catalyzes oxidation of analytes. For example, glucose oxidase can be deposited onto a sensor to enable the sensor to detect glucose.

Sensors employed in amperometry typically include a working electrode, a counter electrode and a reference electrode. In some cases, a sensor includes a working electrode and a combination counter-reference electrode. A number of different technologies can be employed in producing these electrodes. For example, for noble metal thin film electrodes, vacuum deposition including sputtering and evaporation can be employed. These steps can be combined with photolithographic techniques to mask and pattern specific electrodes and connections to the electrodes. For carbon and silver/silver chloride (Ag/AgCl) electrodes, screen printing of the corresponding inks can be employed.

Although human tear typically contains about 0.1 millimolars (mM) to 0.6 mM of glucose, the reported glucose dynamic range spans from 0.01 mM to a few mM, well over two orders of magnitude By contrast, human blood glucose concentration is much higher but covers a much narrow dynamic range (5 to 8 mM for healthy population, 3 to 30 for diabetic population). As such, glucose sensing from the human tear presents special challenges.

First, the wide dynamic range of glucose concentrations requires the sensor controlling and measuring circuitry to be able to handle such a wide range of current. Circuit complexity is thus increased and measurement inaccuracy could occur as such.

Second, the low absolute glucose concentration in a tear requires the sensor to be highly sensitive.

Third, because the sensor current can vary widely, it is useful to have a sensor that can adapt to changing conditions (e.g., concentration fluctuations, background responses, sensor aging). Increasing sensitivity of the sensor can be performed by reducing thickness of an enzyme-protecting membrane layer. However, reducing thickness of the enzyme-protecting membrane layer can be problematic because noise and interference to the sensor would be increased due to reduced membrane filtering ability. In addition, enzyme stability can be compromised.

Accordingly, a sensor that can adapt to these changing conditions (e.g., dynamic change in concentrations, sensor stability, and background noise) is highly desirable. Disclosed herein is a technique wherein the sensor area (and thus sensor sensitivity) can be dynamically adjusted to adapt the changes.

The apparatus, systems and methods relate to contact lenses that include amperometric electrochemical sensors having a working electrode composed of multiple sub-electrodes. The sub-electrodes can be activated or de-activated to adjust sensitivity of the sensors. For example, these sub-electrodes can be controlled by a circuit that can switch a number of the sub-electrodes on or off to a potentiostat. When glucose level in tear fluid is low, more sub-electrodes can be turned on so that the resulting current signal generated by the circuit is higher than otherwise generated when only one electrode is used. When glucose level in tear fluid is high, fewer sub-electrodes are turned on so that likelihood that the resulting current overflows or saturates the measurement circuit is mitigated or eliminated.

In one aspect, a method is provided. The method includes: detecting level of at least one of an analyte or biological substance on a contact lens; and activating a number of sub-electrodes of a sensor based, at least, on the level of the analyte or biological substance, wherein the activating the number of the sub-electrodes adjusts sensitivity of the sensor.

In another aspect, a method is provided. The method includes: detecting level of output current of an electrochemical sensor of a contact lens; and activating a number of sub-electrodes of a sensor based, at least, on the level of the output current, wherein the activating the number of the sub-electrodes adjusts a sensitivity of the sensor.

In another aspect, a contact lens is provided. The contact lens includes: a substrate; a power component, disposed on or within the substrate, configured to output power; a circuit; and an adjustment circuit. The circuit can include: a potentiostat, disposed on or within the substrate, and configured to be powered by the power component; and a sensor, disposed on or within the substrate, electrically coupled to the potentiostat, and configured to sense level of an analyte in an eye over which the contact lens is worn, wherein sensitivity of the sensor is adjustable. The adjustment circuit can be disposed on or within the substrate, electrically coupled to the sensor, and configured to control the sensitivity of the sensor.

In another aspect, yet another contact lens is provided. The contact lens can include: an adjustment circuit and a measurement circuit. The adjustment circuit can be configured to adjust level of sensitivity of a sensor of the contact lens. The measurement circuit can be configured to: determine current output from the sensor, wherein the sensor comprises a plurality of sub-electrodes of a working electrode; determine whether the current meets a predefined condition for adjustment of a number of the plurality of sub-electrodes, wherein adjustment comprises activation or de-activation of at least one of the plurality of the sub-electrodes; and output a feedback signal to the adjustment circuit in response to the predefined condition being met, wherein the feedback signal includes at least one of information indicative of a level associated with the current output from the sensor or information indicative of an adjustment to be performed by the adjustment circuit.

In another aspect, an electrode system is provided. The electrode system can include: a counter electrode of an electrochemical sensor of a contact lens; and a working electrode of the electrochemical sensor. The working electrode can include a plurality of sub-electrodes configured to be turned on or off. The electrode system is configured to increase sensing sensitivity with an increase in a number of the plurality of sub-electrodes turned on and decrease sensing sensitivity with a decrease in a number of the plurality of sub-electrodes turned off.

One or more of the aspects described herein can enable sensing of glucose from tear fluid via a contact lens. Specifically, one or more aspects can enable calibration of the number of sub-electrodes in a sensor. As such, the sensor can output a current amount that corresponds to a known amount of glucose. In some aspects, the current output from the sensor is controlled to be within a range of a measurement circuit produced by a manufacturer (as opposed to outputting a current to the measurement circuit that is too high or too low and unable to be detected and/or measured by the measurement circuit) is increased. In some aspects, the range of sensor output current for the small range of glucose concentrations is increased to at least one order of magnitude.

Turning first to FIG. 1, an illustration of a block diagram of an exemplary non-limiting system that facilitates contact lenses having sensors with adjustable sensitivity is shown. The system 100 can include a contact lens 102 having at least one electrochemical sensor 108 with adjustable sensitivity. In some aspects, the system 100 can also include radio frequency (RF) reader 120.

As shown, contact lens 102 can cover at least a portion of eye 104 and can include the sensor 108, adjustment circuit 110, measurement circuit 112, potentiostat 114, communication component 116 and/or power component 118. The sensor 108, adjustment circuit 110, measurement circuit 112, potentiostat 114, communication component 116 and/or power component 118 can be communicatively or electrically coupled to one another to perform one or more of the functions of the contact lens 102. For example, the components can be communicatively or electrically coupled to one another to perform sensing, adjustment of the sensor 108, applying potential to the sensor 108, outputting power, facilitating communication and/or measurement of current.

The sensor 108 can sense an analyte concentration of a solution on or within the contact lens 102. While the aspects described herein will employ glucose sensing, in various aspects, the analyte can be glucose, protein, triglycerides, urea, lactate and/or any number of other different types of analytes.

The sensor 108 can be an amperometric electrochemical sensor. In some aspects, the sensor 108 can include, at least, a working electrode and combination counter-reference electrode. In some aspects, the counter and reference can be separate electrodes. Functions of the sensor 108 can include sensing the analyte concentration of a solution incident on the contact lens 102.

The working electrode can be composed of a plurality of sub-electrodes, and can facilitate determination of the analyte concentration. For example, in some aspects, an enzyme can be deposited on the sub-electrodes to enable the sensor 108 to sense its substrates. For example, in some aspects, glucose oxidase can be deposited on the sub-electrodes of the sensor 108. The sensor 108 can then become a glucose biosensor. As such, the glucose biosensor can sense concentration of glucose in a body of the wearer of the contact lens 102.

The adjustment circuit 110 can include a plurality of switches that can respectively couple to the sub-electrodes to create an electrical connection between the potentiostat 114 and the respective sub-electrode. The potentiostat 114 can be configured to apply a potential to one or more of the sub-electrodes to cause the sub-electrode to generate current when glucose is detected by the sensor 108. The current can be measured by the measurement circuit 112.

Accordingly, when the adjustment circuit 110 opens the switch, the sub-electrode corresponding to the switch is turned off (de-activated). Similarly, when the adjustment circuit 110 closes the switch, the sub-electrode corresponding to the switch is turned on (activated). As such, the adjustment circuit 110 can individually turn on (activate) or turn off (de-activate) the sub-electrodes of the working electrode.

As the number of sub-electrodes turned on increases, sensitivity of the sensor 108 can increase. As the number of sub-electrodes turned on decreases, sensitivity of the sensor 108 can decrease. Accordingly, the adjustment circuit 110 can adjust sensitivity of the sensor 108.

For example, if glucose concentration level in fluid on the contact lens 102 is determined to be at a low level, the adjustment circuit 110 can increase sensitivity of the sensor 108 by increasing the number of sub-electrodes electrically coupled to the corresponding switches of the adjustment circuit 110. The resultant current output from the sensor 108 can be amplified with an increase in sub-electrodes turned on, and the current measurement performed by the measurement circuit 112 can be more reliable (relative to aspects wherein the number of sub-electrodes activated is not increased).

Similarly, if the glucose concentration level in fluid on the contact lens 102 is at a second level determined to be a high level, the adjustment circuit 110 can decrease sensitivity of the sensor 108 by decreasing the number of sub-electrodes electrically coupled to the corresponding switches of the adjustment circuit 110. The resultant current output from the sensor 108 can decline with a decrease in sub-electrodes turned on, and the current output from the sensor 108 to the measurement circuit 112 can be therefore less likely to oversaturate the measurement circuit 112 (relative to aspects wherein the number of sub-electrodes is not decreased).

In various different aspects, the adjustment circuit 110 can perform static or dynamic adjustment of sensitivity of the sensor 108. For example, the adjustment circuit 110 can perform static adjustment of the sensor 108. The adjustment circuit 110 can activate or de-activate a particular number of sub-electrodes a single time in advance of or during the first operation of the contact lens 102.

This calibration can be based on maximum or minimum current that can be received and read by the measurement circuit 112 and/or the past or average glucose concentration levels of the wearer of the contact lens. For example, the adjustment circuit 110 can activate a particular number of sub-electrodes that provides an output current from the sensor 108 that is less than the maximum current that can be received and read by the measurement circuit 112 without oversaturation.

As another example, the adjustment circuit 110 can activate a number of sub-electrodes that provides an output current that is within a range typical of that generated in the past for the wearer of the contact lens 102. For example, if the wearer of the contact lens 102 typically has high glucose levels, the adjustment circuit 110 can calibrate the sensor 108 with a small number of sub-electrodes (e.g., 1 or 2) activated to reduce the chance of oversaturation of the measurement circuit 112.

In lieu of performing static adjustment, in some aspects, the adjustment circuit 110 can dynamically adjust sensitivity of the sensor 108. For example, the adjustment circuit 110 can dynamically and continually (or, in some aspects, continuously) activate or de-activate a particular number of sub-electrodes based on current measurements made by the measurement circuit 112.

For example, the measurement circuit 112 can continually (or, in some aspects, continuously) monitor the current being output from the sensor 108. In some aspects, the measurement circuit 112 can output a feedback signal based on the measured current.

The feedback signal can be input to a device that can compare the value of the current measured to one or more reference values. If the current value is too high (e.g., higher than a first reference value), the measurement circuit 112 can output a signal to the adjustment circuit 110 to cause the adjustment circuit 110 to reduce the number of activated sub-electrodes. By contrast, if the current value is too low (e.g., lower than a second reference value), the measurement circuit 112 can output a signal to the adjustment circuit 110 to cause the adjustment circuit 110 to increase the number of activated sub-electrodes.

In some aspects, adjustment can be provided in advance of undesirable current conditions. For example, past current values can be measured over time by the measurement circuit 112 and stored in memory. The logic circuitry can compare the current values over time and determine whether there is a trend showing an increase in current values or a decrease in current values such that the current is expected to reach a level that would either oversaturate the measurement circuit 112 or that the measurement circuit 112 cannot accurately measure. If the current begins to approach the maximum current that can be read/received by the measurement circuit 112, the adjustment circuit 110 can dynamically de-activate a number of sub-electrodes to reduce the output current.

For example, the current received can be between 1 nA and 100 nA in some aspects. If the current begins to approach 100 nA, for example, the adjustment circuit 110 can adjust the number of sub-electrodes activated to reduce the current to a value that is within an acceptable current value range for the measurement circuit 112.

The number of sub-electrodes to activate or de-activate can be determined on the contact lens in some aspects. For example, each sub-electrode can be considered to contribute a maximum sensor current. Accordingly, in some aspects, the number of sub-electrodes activated can be the number that, should the sub-electrodes output the maximum current, the total current output will be less than the maximum current that can be received and read by the measurement circuit 112 without oversaturation.

As another example, the adjustment circuit 110 can dynamically activate or de-activate a particular number of sub-electrodes based on current measurements continually made by the measurement circuit 112 as noted above. However, the contact lens can transmit information indicative of the current measured by the measurement circuit 112 to a device external to the contact lens (e.g., RF reader 120 of FIG. 1). For example, in some aspects, the contact lens can include a communication component 116 that can communicate information wirelessly between the contact lens and a device external to the contact lens.

The device external to the contact lens can receive the information indicative of the current measured by the measurement circuit 112 and perform a calculation to determine the number of sub-electrodes that should be activated (or de-activated) to achieve a desired current. The device can transmit adjustment information back to the contact lens 102 for adjustment of the number of sub-electrodes that are activated/de-activated. For example, information indicative of a number of sub-electrodes to activate or de-activate can be transmitted to the contact lens 102. The adjustment circuit 110 can then adjust the number of sub-electrodes accordingly.

As yet another example, as described above, the adjustment circuit 110 can dynamically activate or de-activate a particular number of sub-electrodes based on the level of concentration of the material being sensed by the contact lens. For example, if the glucose concentration level being sensed is low, the number of sub-electrodes activated can be increased so as to cause the sensor 108 to generate more current for the low glucose concentration. By contrast, if the glucose concentration level being sensed is high, the number of sub-electrodes activated can be decreased so as to reduce the likelihood of oversaturation of the measurement circuit 112. Accordingly, embodiments herein can adjust sensitivity of the sensor 108 and/or reduce the likelihood of oversaturation of the measurement circuit 204.

In some aspects, adjustment can be provided in advance of undesirable concentration conditions. For example, past concentration values can be measured over time by the measurement circuit 112 and stored in memory. The logic circuitry can compare the values over time and determine whether there is a trend showing an increase in concentration values or a decrease in concentration values such that the concentration is expected to reach a level that would either cause the sensor 108 to generate a current resulting in oversaturation of the measurement circuit 112 or that the measurement circuit 112 cannot accurately measure.

If the concentration begins to approach the maximum concentration that can be read/received by the measurement circuit 112, the adjustment circuit 110 can dynamically de-activate a number of sub-electrodes to reduce the corresponding output current. Similarly, if the concentration begins to approach the minimum concentration that can be read/received by the measurement circuit 112, the adjustment circuit 110 can dynamically activate a number of sub-electrodes to increase the corresponding output current.

The communication component 116 can be configured to communicate information from or receive information at the contact lens 102. For example, the communication component 116 can communicate information 122 (e.g., a glucose concentration level and/or a current level corresponding to sensed glucose) from the contact lens 102 to a device external to the contact lens 102. By way of example, but not limitation, the communication component can be or include an RF antenna, and can be configured to communicate with an RF reader 120 external to the contact lens 102. In various aspects, the communication component 116 can generally include a transmitter and receiver and/or transceiver configured to communicate via wireless or optical communication.

It is to be appreciated that in accordance with one or more aspects described in this disclosure, users can opt-in or opt-out of providing personal information, demographic information, location information, proprietary information, sensitive information, or the like in connection with data gathering aspects. Moreover, one or more aspects described herein can provide for anonymizing collected, received, or transmitted data.

In some aspects, the contact lens 102 can include memory (not shown) and/or logic circuitry (not shown). The memory can store information regarding the analyte concentration sensed, output currents and/or computer-executable instructions for execution by the logic circuitry. The logic circuitry can execute computer-executable instructions to perform one or more functions of the contact lens 102. For example, in some aspects, the logic circuitry can convert the output current from the sensor 108 to an analyte concentration value.

Figure 2:
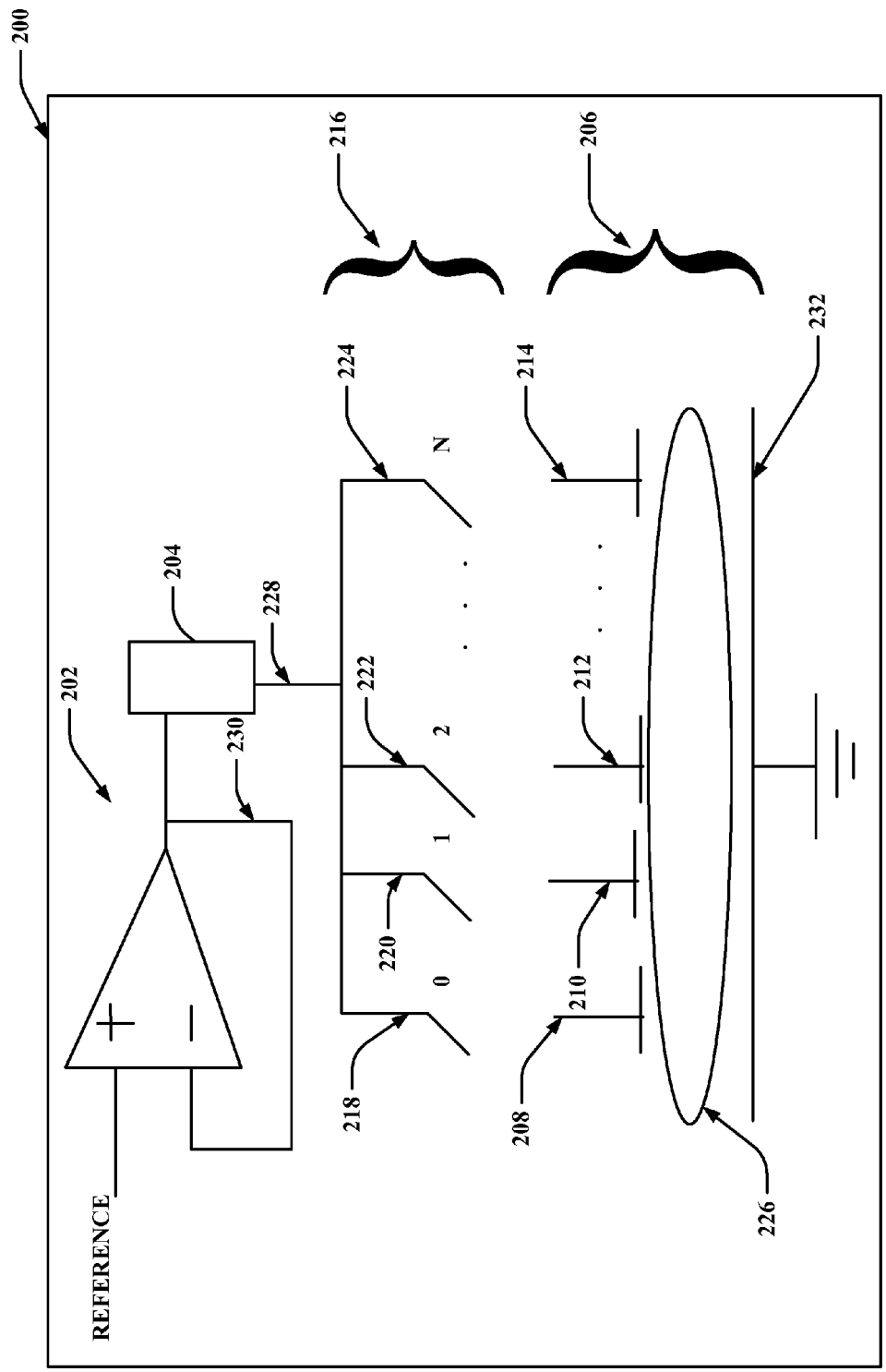
FIG. 2 is an illustration of an exemplary non-limiting diagram of a circuit for a contact lens having a sensor with adjustable sensitivity in accordance with aspects described herein.

FIG. 2 is an illustration of an exemplary non-limiting diagram of a circuit for a contact lens having a sensor with adjustable sensitivity in accordance with aspects described herein.

The circuit 200 includes a potentiostat 202, measurement circuit 204, a sensor 206 having a working electrode composed of a number of sub-electrodes 208, 210, 212, 214 and a combination counter-reference electrode 232, and an adjustment circuit 216. The adjustment circuit 216 can have a number of switches 218, 220, 222, 224 respectively able to electrically coupled to (or de-coupled from) sub-electrodes 208, 210, 212, 214 (of a working electrode) to turn on (activate) or turn off (de-activate) sub-electrodes 208, 210, 212, 214. Solution 226 can include glucose and can be sensed by sensor 206.

As described in detail with reference to FIG. 1, the sensor 206 can detect a level of glucose in solution 226 employing one or more activated sub-electrodes 208, 210, 212, 214 in contact with solution 226. The adjustment circuit 216 can activate or de-activate various sub-electrodes 208, 210, 212, 214 by electrically coupling (or de-coupling) the switches 218, 220, 222, 224 to (or from) respective sub-electrodes 208, 210, 212, 214. For example, to activate sub-electrode 208 of sensor 206, the adjustment circuit 216 can close switch 218 thereby enabling potentiostat 202 to apply a potential to the sub-electrode 208 to cause the sub-electrode 208 to generate a current 228 when glucose is detected in solution 226. Accordingly, as the number of activated sub-electrodes 208, 210, 212, 214 increases, the current 228 output from the sensor 206 increases. The current 228 can be measured by measurement circuit 204.

In various aspects, the adjustment circuit 216 can activate or de-activate different numbers of sub-electrodes 208, 210, 212, 214 based on different conditions and/or to reduce the chance of oversaturation of the measurement circuit 204, to adjust the sensitivity of the sensor 206 such that low glucose concentration levels are accurately detected and/or to improve the likelihood that the output current from the sensor 206 will be within a measurable range of the measurement circuit 204.

For example, the adjustment circuit 216 can activate or de-activate a particular number of sub-electrodes 208, 210, 212, 214 a single time in advance of or during the first operation of the contact lens on which the circuit 200 is provided. The calibration can be based on the maximum or minimum current that can be received and read by the measurement circuit 204 and/or the past or average glucose concentration level of the wearer of the contact lens. For example, the adjustment circuit 216 can activate a number of sub-electrodes that provides a sensor output current that is less than the maximum current and greater than the minimum current that can be received and read by the measurement circuit without oversaturation. As another example, the adjustment circuit 216 can activate a number of sub-electrodes that provides a sensor output current that is within a range that is typical of that generated in the past for the wearer of the contact lens. Estimated future glucose concentration levels can be determined based on past or average glucose concentration levels for the wearer of the contact lens.

As another example, the adjustment circuit 216 can dynamically activate or de-activate a particular number of sub-electrodes 208, 210, 212, 214 based on measurements continually made by the measurement circuit 204. For example, the measurement circuit 204 can continually monitor the current 228 being output from the sensor 206. In some aspects, the measurement circuit 204 can output a feedback signal 230 that can be input to a device that can compare the current 228 to a reference as shown in FIG. 2.

If the current 228 is too great, the measurement circuit 204 can output a signal that causes the adjustment circuit 216 to reduce the number of activated sub-electrodes. If the current 228 is too low, the measurement circuit 204 can output a signal that causes the adjustment circuit 216 to increase the number of activated sub-electrodes.

In some aspects, adjustment can be provided in advance of undesirable current conditions. For example, if the current 228 begins to approach the maximum current that can be read/received by the measurement circuit 204, the adjustment circuit 216 can dynamically de-activate a number of sub-electrodes to reduce the output current 228. For example, the current 228 received can be between 1 nA and 100 nA in some aspects. If the current 228 begins to approach 100 nA, for example, the adjustment circuit 216 can adjust the number of sub-electrodes activated to reduce the current 228 to a value that is less than the value prior to adjustment.

The number of sub-electrodes to activate or de-activate can be determined on the contact lens in some aspects. For example, each sub-electrode can be considered to contribute a maximum sensor current. Accordingly, in some aspects, the number of sub-electrodes activated can be the number that, should the sub-electrodes output the maximum current, the total current output will be less than the maximum current that can be read/received by the measurement circuit 204 without oversaturation.

As another example, the adjustment circuit 216 can dynamically activate or de-activate a particular number of sub-electrodes 208, 210, 212, 214 based on measurements continually made by the measurement circuit 204 as noted above.

However, in some aspects, the contact lens can transmit information indicative of the current 228 measured by the measurement circuit 204 to a device external to the contact lens (e.g., RF reader 120 of FIG. 1). For example, in some aspects, the contact lens can include a communication component (not shown) that can communicate information wirelessly between the contact lens and a device external to the contact lens.

The device external to the contact lens can receive the information indicative of the current 228 measured by the measurement circuit 204 and perform a calculation to determine the number of sub-electrodes that should be activated to achieve a desired current. The device can transmit adjustment information back to the contact lens for adjustment of the number of sub-electrodes that are activated/de-activated. For example, information indicative of a number of sub-electrodes to activate or de-activate can be transmitted to the contact lens. The adjustment circuit 216 can then adjust the number of sub-electrodes accordingly.

As yet another example, the adjustment circuit 216 can dynamically activate or de-activate a particular number of sub-electrodes 208, 210, 212, 214 based on the level of concentration of the material being sensed by the contact lens. For example, if the glucose concentration level being sensed is low, the number of sub-electrodes activated can be increased so as to cause the sensor 206 to generate more current 228 for the low glucose concentration. By contrast, if the glucose concentration level being sensed is high, the number of sub-electrodes activated can be decreased so as to not oversaturate the measurement circuit 204. Accordingly, embodiments herein can adjust sensitivity of the sensor 206 and/or reduce the likelihood of saturation of the measurement circuit 204.

Although not shown, circuit 200 can include or be coupled to a power component that can output power to the circuit 200 (or to components within the circuit 200). For example, a power component can output power to the sensor 206, adjustment circuit 216, measurement circuit 204 and/or potentiostat 202.

In some aspects, the circuit 200 can include (or be communicatively or electrically coupled to) a memory (not shown) and/or logic circuitry (not shown) on the contact lens. The memory can be a computer-readable storage medium storing computer-executable instructions and/or information for performing the functions described in this disclosure with reference to the contact lens and/or circuit 200. For example, the memory can include past or average sensor current outputs, glucose concentrations, a number of sub-electrodes to be activated or de-activated based on past or predefined conditions, amounts of current typically output from an activated sub-electrode that senses glucose of various different concentrations and the like.

The circuit 200 and/or contact lens can also include logic circuitry for performing one or more functions of the contact lens and/or circuit 200. For example, calculations to determine the number of sub-electrodes to activate or de-activate can be facilitated via the logic circuitry.

Figure 3:
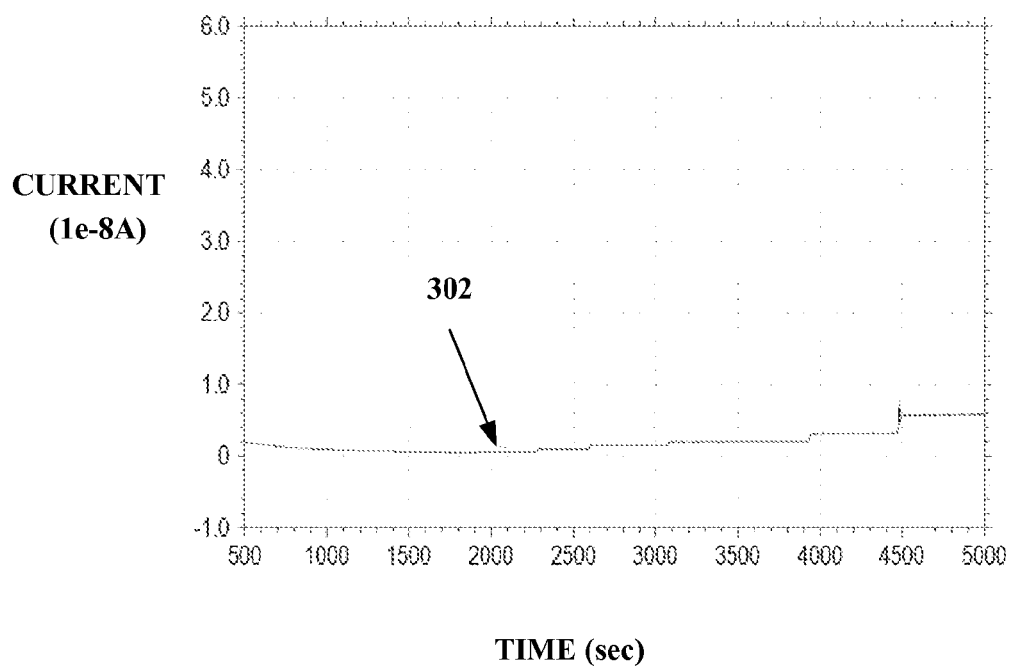
FIG. 3 is an illustration of an exemplary non-limiting graph detailing the performance of a glucose sensor with a single working electrode in accordance with aspects described herein.

The performance of glucose sensors with a single working electrode and with multiple sub-electrodes are described with reference to FIGS. 3 and 4. Turning first to FIG. 3, an illustration of an exemplary non-limiting graph detailing the performance of a glucose sensor with a single working electrode is shown. The glucose sensor can include the functionality and/or the structure of the sensor (e.g., sensor 206) described herein in various aspects.

The glucose sensor includes a single working electrode of dimensions 25 microns ($\mu$m)×1 millimeter (mm). The output current from the glucose sensor at different glucose concentrations in a phosphate buffered saline (PBS) solution at 35 degrees Celsius (° C.) is shown. In the embodiment shown, a potentiostat model number CHI 1030B from CH Instruments was employed to control the potential of the working electrode to be 600 millivolts (mV) more positive than the potential at the Ag/AgCl combination counter-reference electrode. The sensor on the contact lens had a 15 $\mu$m poly(vinyl pyridine-HEMA) hydrogel layer membrane.

The results are shown for a glucose concentration of 50 $\mu$m. With a single electrode, sensor output current value 302 was approximately 0.1-0.2 nA. Accordingly, at low glucose concentration levels, with only a single working electrode as part of the sensor, the output sensor current signal was too low to be measured accurately.

Figure 4:
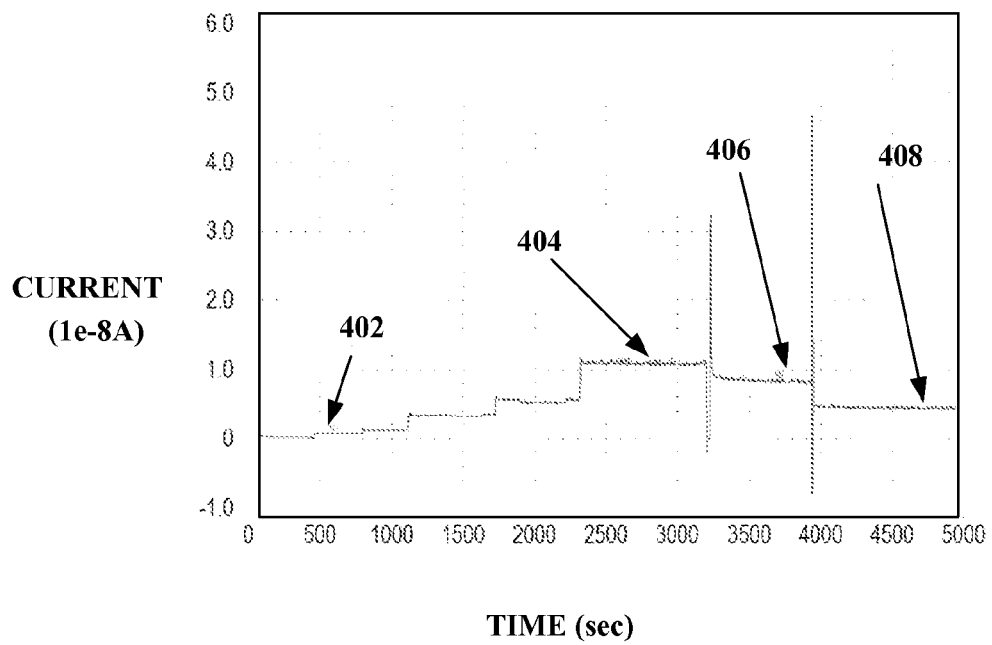
FIG. 4 is an illustration of an exemplary non-limiting graph detailing the performance of a glucose sensor with three switchable sub-electrodes of the working electrode in accordance with aspects described herein.

The sensitivity of the sensor can be increased by adding additional sub-electrodes and coupling the additional sub-electrodes to the potentiostat, as described and shown with reference to FIG. 4.

FIG. 4 is an illustration of an exemplary non-limiting graph detailing the performance of a glucose sensor with three switchable sub-electrodes of the working electrode in accordance with aspects described herein. The glucose sensor can include the functionality and/or the structure of the sensor (e.g., sensor 206) described herein in various aspects.

The glucose sensor included a working electrode with three sub-electrodes. The dimensions of each of the three sub-electrodes was 25 microns ($\mu$m)×1 millimeter (mm) The other conditions were the same as described with reference to FIG. 3.

The results are shown for different glucose concentrations and while different numbers of the three sub-electrodes were turned on to the potentiostat. For example, with three sub-electrodes turned on, and at a glucose concentration of 50 $\mu$m, the sensor output current value 402 was approximately 0.9 nA (instead of sensor output current value 302, which was approximately 0.1-0.2 nA with the same glucose concentration of 50 $\mu$m but only a single working electrode). Thus, by using three sub-electrodes instead of one, the sensor output current at low glucose levels (e.g., 50 $\mu$m) was increased to a level that facilitates measurement (e.g., a level close to 1 nA).

As the glucose concentration increased, if the number of sub-electrodes that were turned on was held constant, the sensor output current increased. For example, with three sub-electrodes turned on, and a glucose concentration of 1000 $\mu$m, the sensor output current value 404 was approximately 11.5 nA.

If desired, this current can be reduced at the same high glucose concentration. For example, with only two sub-electrodes turned on (instead of three sub-electrodes turned on), the sensor output current value 406 changed to approximately 8.0 nA. The sensitivity of the sensor can be further reduced by turning on one sub-electrode to the potentiostat. As shown at 406, when the number of sub-electrodes was reduced to one, the sensor output current value 408 was lowered to 5.5 nA. As shown, at higher glucose levels, the sensor output current can be decreased by reducing the number of sub-electrodes activated. As such, the likelihood of oversaturation of the current measurement circuit can also be reduced.

As shown in FIG. 4, the number of sub-electrodes in a sensor activated can be adjusted to enable the sensor to output a current amount to avoid reaching a current ceiling or floor and thereby not having a current output that corresponds to the true glucose concentration. As also shown in FIG. 4, the current output from the sensor can be controlled to be within a range of a measurement circuit produced by a manufacturer (as opposed to outputting a current to the measurement circuit that is too high or too low and unable to be detected and/or measured by the measurement circuit). As also shown in FIG.

4, the range of sensor output current for the small range of glucose concentrations is increased by at least one order of magnitude.

FIGS. 5, 6, 7 and 8 are illustrations of exemplary non-limiting flow diagrams of methods that facilitate contact lenses having sensors with adjustable sensitivity in accordance with aspects described herein.

Figure 5:
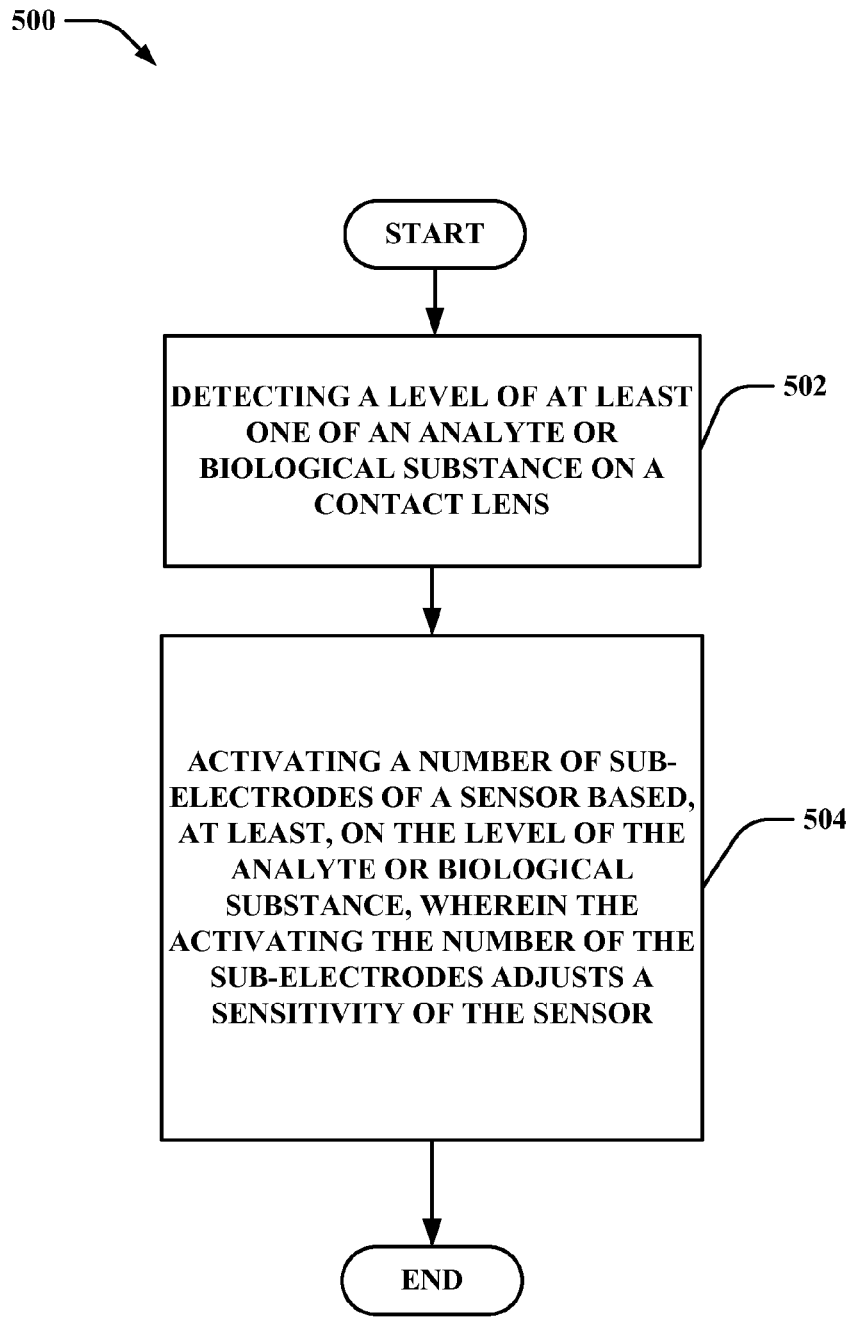
FIGS. 5, 6, 7 and 8 are illustrations of exemplary non-limiting flow diagrams of methods that facilitate contact lenses having sensors with adjustable sensitivity in accordance with aspects described herein.

Turning first to FIG. 5, at 502, method 500 can include detecting a level of at least one of an analyte or biological substance on a contact lens (e.g., using the sensor 206). For example, a sensor can perform detection via one or more of a plurality of sub-electrodes of a working electrode of the sensor. In some aspects, the analyte or biological component is glucose. However, in various other aspects, the analyte and/or biological component can include, but is not limited to, lactate, urea, hydrogen ions or cholesterol or alcohol.

At 504, method 500 can include activating a number of sub-electrodes of a sensor based, at least, on the level of the analyte or biological substance, wherein the activating the number of the sub-electrodes adjusts a sensitivity of the sensor (e.g., using the adjustment circuit 216). As the number of sub-electrodes turned on increases, the sensitivity to a particular sensed concentration level can increase. Similarly, as the number of sub-electrodes turned on decreases, the sensitivity to a particular sensed concentration level can decrease.

In some aspects, a first number of sub-electrodes can be turned on in response to a first level of the analyte or biological substance being sensed, and a second number of sub-electrodes can be turned on in response to a second level of the analyte or biological substance being sensed. In some aspects, the concentration of analyte or biological substance can be less than a first threshold value and, as a result, the number of sub-electrodes can be increased to improve detection of the analyte or biological component. In some aspects, the concentration of analyte or biological substance can be greater than or equal to a second threshold value and, as a result, the number of sub-electrodes can be decreased to reduce the likelihood of oversaturation of the measurement circuit.

In some aspects, the past concentration levels can be employed to determine whether a trend of increasing or decreasing concentration levels exists. If a trend exists, the number of sub-electrodes turned on can be adjusted to reduce the likelihood that the concentration level will be undetectable (or will generate a current that will oversaturate the measurement circuit).

Figure 6:
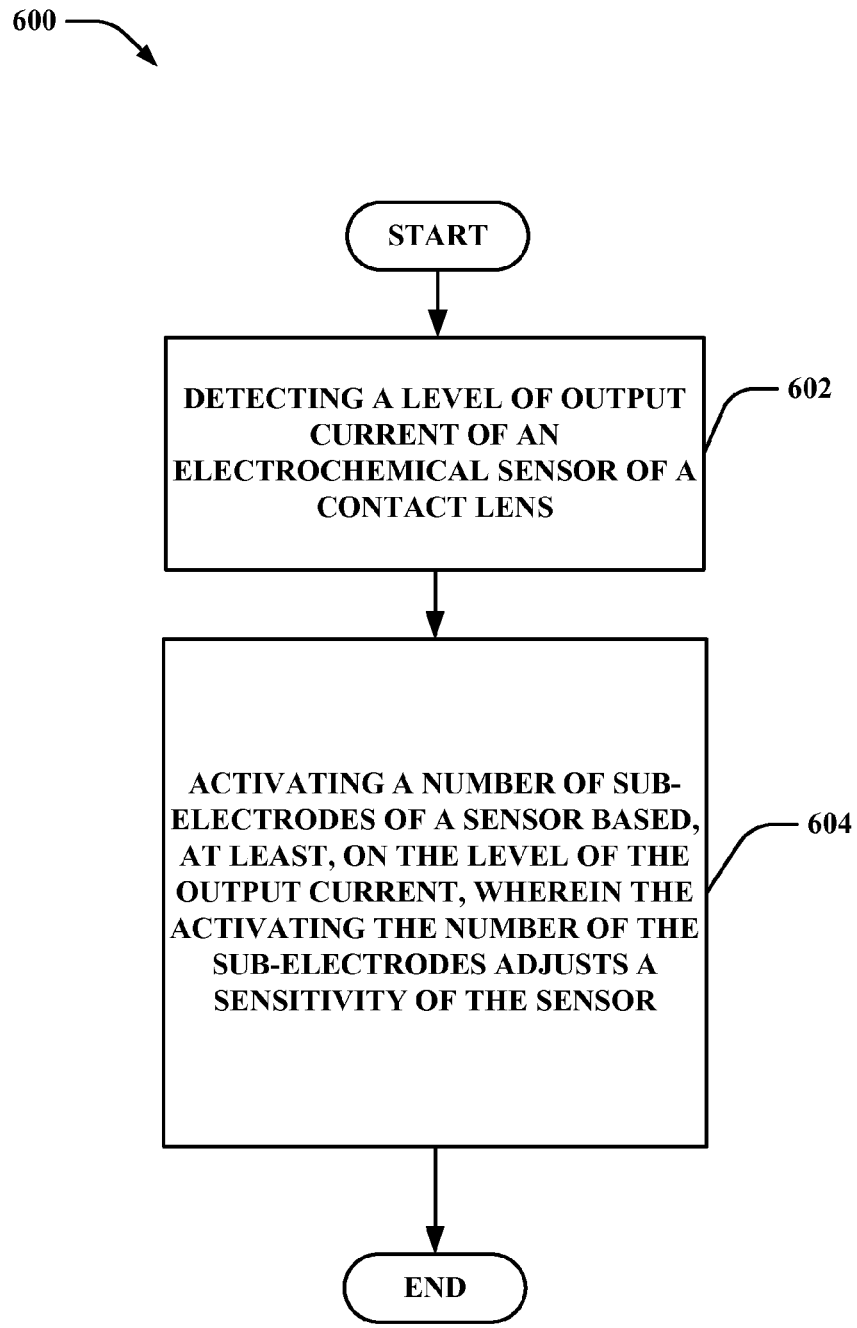

Turning now to FIG. 6, at 602, method 600 can include detecting a level of output current of an electrochemical sensor of a contact lens (e.g., using the measurement circuit 204). For example, a sensor can perform detection of an analyte via one or more of a plurality of sub-electrodes of a working electrode and output a corresponding current. The corresponding current can be measured by the measurement circuit. In some aspects, the analyte or biological component is glucose. However, in various other aspects, the analyte and/or biological component can include, but is not limited to, lactate, urea, hydrogen ions, cholesterol or alcohol.

At 604, method 600 can include activating a number of sub-electrodes of a sensor based, at least, on the level of the output current, wherein the activating the number of the sub-electrodes adjusts sensitivity of the sensor (e.g., using the adjustment circuit 216). As the number of sub-electrodes turned on increases, the output current for a sensed concentration can increase. Similarly, as the number of sub-electrodes turned on decreases, the output current for a sensed concentration can decrease.

In some aspects, a first number of sub-electrodes can be turned on in response to a first current level of being measured, and a second number of sub-electrodes can be turned on in response to a second current level being measured. In some aspects, the past measured current levels can be employed to determine whether a trend of increasing or decreasing current levels exists. If a trend exists, the number of sub-electrodes can be adjusted such that the current levels are within a particular range of the maximum or minimum current that can be received/read by the measurement circuit, the number of sub-electrodes can be adjusted accordingly.

Figure 7:
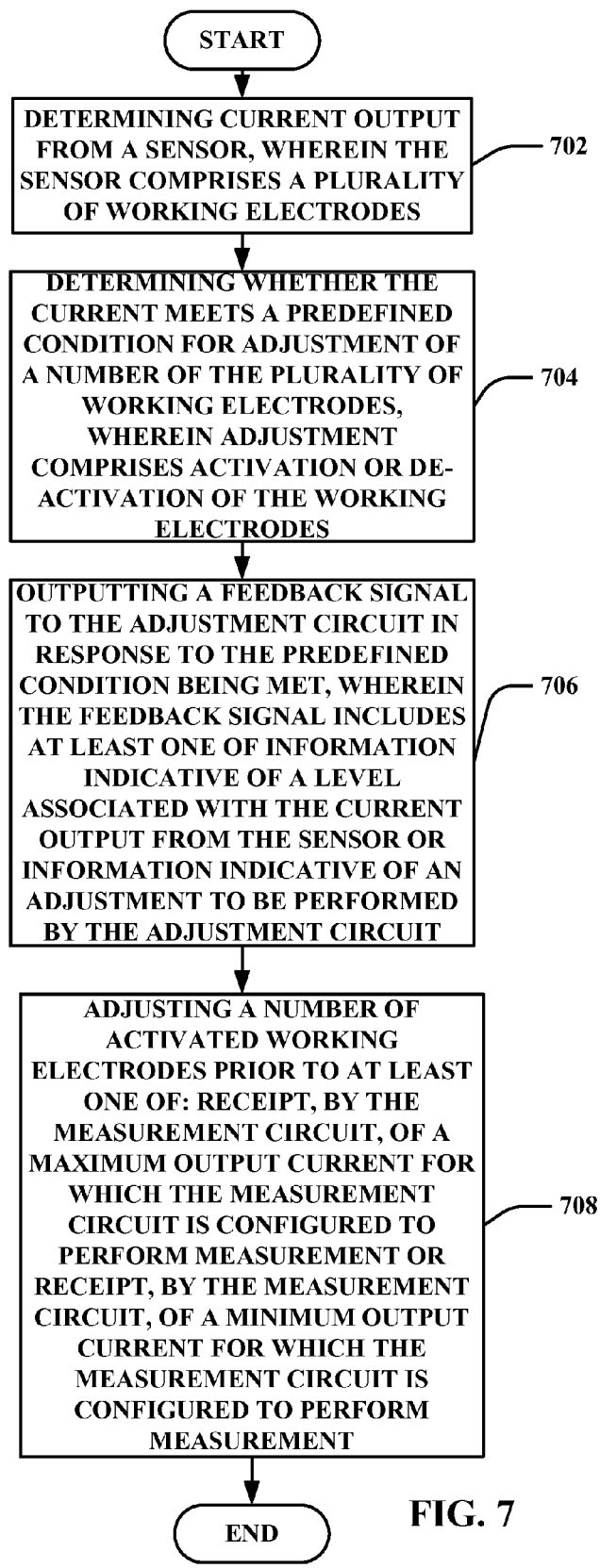

Turning now to FIG. 7, at 702, method 700 can include determining current output from a sensor of a contact lens, wherein the sensor includes a plurality of sub-electrodes of a working electrode (e.g., using the measurement circuit 204). The current can be output as a result of sensing a particular analyte on the contact lens. The current value can correspond to the concentration of the analyte.

At 704, method 700 can include determining whether the current meets a predefined condition for adjustment of a number of the plurality of sub-electrodes, wherein adjustment comprises activation or de-activation of at least one of the plurality of the working electrodes (e.g., using the measurement circuit 204).

In some aspects, the predefined condition can be based on the maximum and minimum current that can be output from the sensor without oversaturating the measurement circuit. For example, if the current is between the maximum and minimum values that can be output from the sensor without oversaturating the measurement circuit, the number of sub-electrodes turned on may not be adjusted. If the current is not between the maximum and minimum values (or if a trend in current values indicates that the current will not be between the maximum and minimum value in the near future), the number of sub-electrodes turned on can be adjusted to increase or decrease the output current to values within the range between the maximum and minimum values.

At 706, method 700 can include outputting a feedback signal to the adjustment circuit in response to the predefined condition being met. The feedback signal can include information indicative of a level associated with the current output from the sensor or information indicative of an adjustment to be performed by the adjustment circuit (e.g., using the measurement circuit 204).

At 708, method 700 can include adjusting a number of activated sub-electrodes prior to at least one of: receipt, by the measurement circuit, of a maximum output current for which the measurement circuit is configured to perform measurement or receipt, by the measurement circuit, of a minimum output current for which the measurement circuit is configured to perform measurement (e.g., using the adjustment circuit 216).

The adjustment circuit can include a number of switches corresponding to respective sub-electrodes. The adjustment circuit can adjust the number of activated sub-electrodes by closing one or more switches of the adjustment circuit thereby allowing a potentiostat to apply potential to the sub-electrode.

Figure 8:
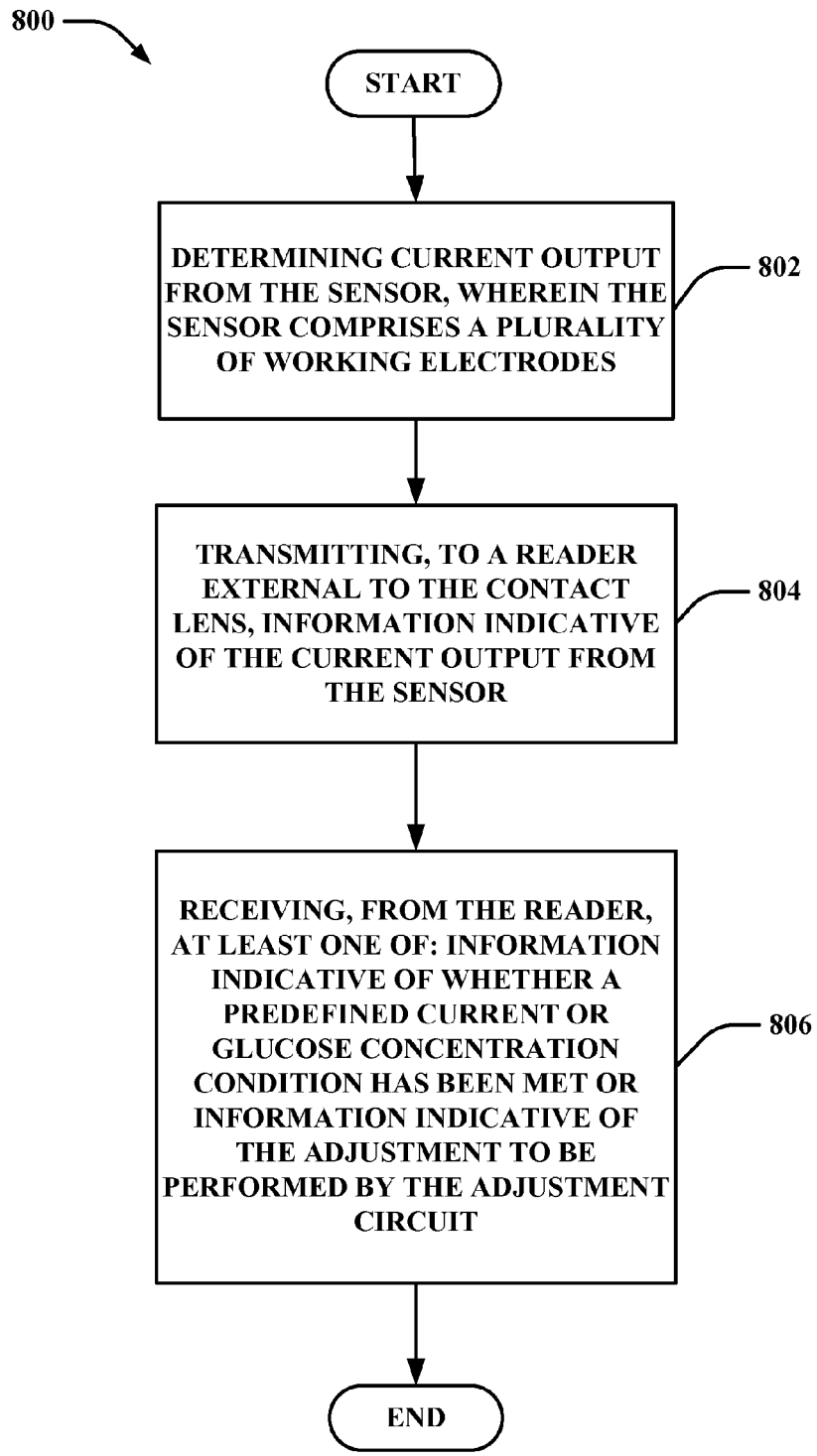

Turning now to FIG. 8, at 802, method 800 can include determining current output from the sensor, wherein the sensor comprises a plurality of sub-electrodes of a working electrode (e.g., using the measurement circuit 204).

At 804, method 800 can include transmitting, to a reader external to the contact lens, information indicative of the current output from the sensor (e.g., using the contact lens 102). For example, the contact lens can transmit the information to a RF reader in geographic proximity to the contact lens.

At 806, method 800 can include receiving, from the reader, at least one of: information indicative of whether a predefined current or glucose concentration condition has been met or information indicative of the adjustment to be performed by the adjustment circuit (e.g., using the contact lens 102).

Exemplary Networked and Distributed Environments

Figure 9:
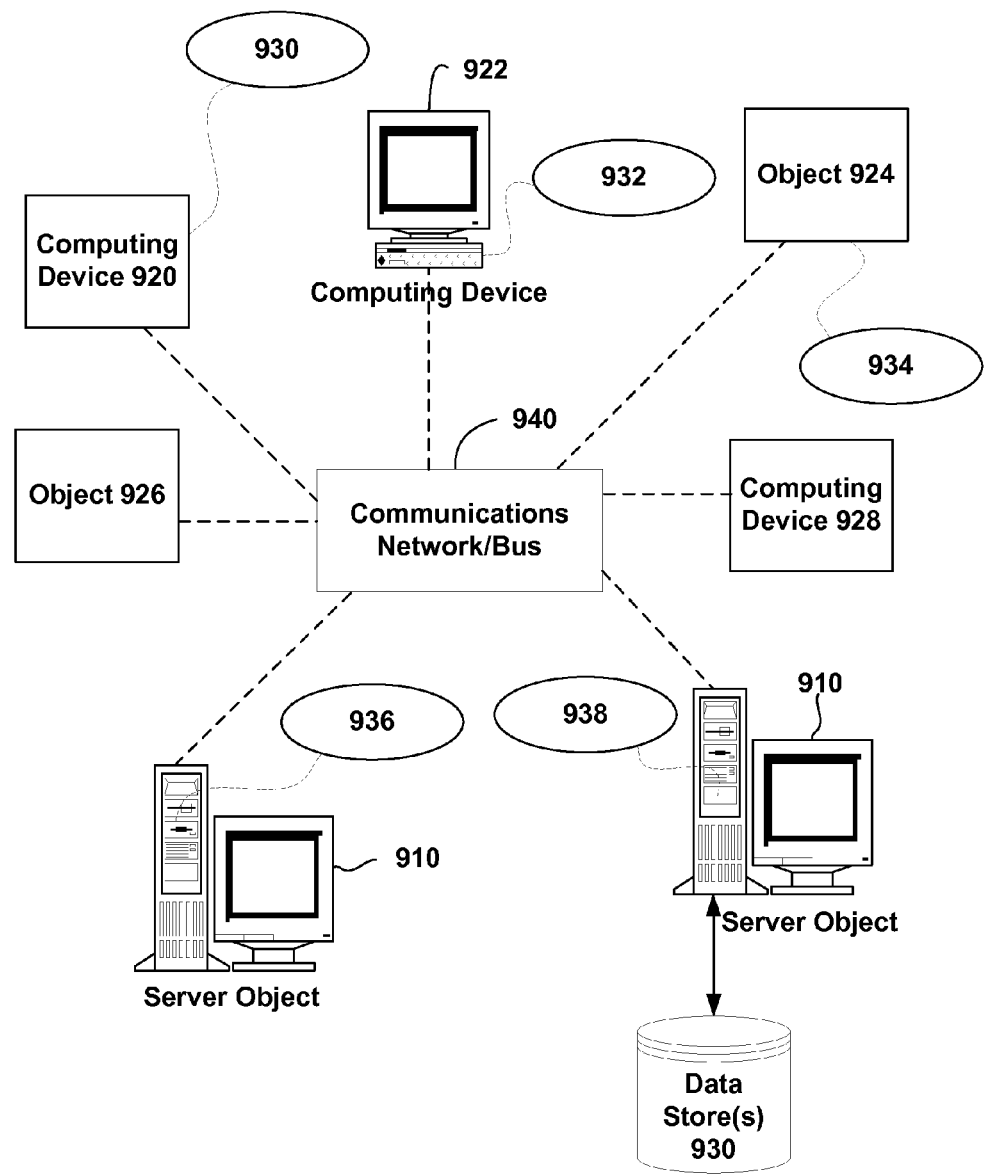
FIG. 9 is an illustration of a schematic diagram of an exemplary networked or distributed computing environment with which one or more aspects described herein can be associated.

FIG. 9 provides a schematic diagram of an exemplary networked or distributed computing environment with which one or more aspects described in this disclosure can be associated. The distributed computing environment includes computing objects 910, 912, etc. and computing objects or devices 920, 922, 924, 926, 928, etc., which can include programs, methods, data stores, programmable logic, etc., as represented by applications 930, 932, 934, 936, 938. It can be appreciated that computing objects 910, 912, etc. and computing objects or devices 920, 922, 924, 926, 928, etc. can include different devices, such as active contact lenses (and components thereof), personal digital assistants (PDAs), audio/video devices, mobile phones, MPEG-1 Audio Layer 3 (MP3) players, personal computers, laptops, tablets, etc.

Each computing object 910, 912, etc. and computing objects or devices 920, 922, 924, 926, 928, etc. can communicate with one or more other computing objects 910, 912, etc. and computing objects or devices 920, 922, 924, 926, 928, etc. by way of the communications network 940, either directly or indirectly. Even though illustrated as a single element in FIG. 9, network 940 can include other computing objects and computing devices that provide services to the system of FIG. 9, and/or can represent multiple interconnected networks, which are not shown.

In a network environment in which the communications network/bus 940 can be the Internet, the computing objects 910, 912, etc. can be Web servers, file servers, media servers, etc. with which the client computing objects or devices 920, 922, 924, 926, 928, etc. communicate via any of a number of known protocols, such as the hypertext transfer protocol (HTTP).

Exemplary Computing Device

As mentioned, advantageously, the techniques described in this disclosure can be associated with any suitable device. In various aspects, the data store can include or be included within, any of the memory described herein and/or any of the contact lenses described herein. In various aspects, the data store can be any repository for storing information transmitted to or received from the contact lens.

Figure 10:
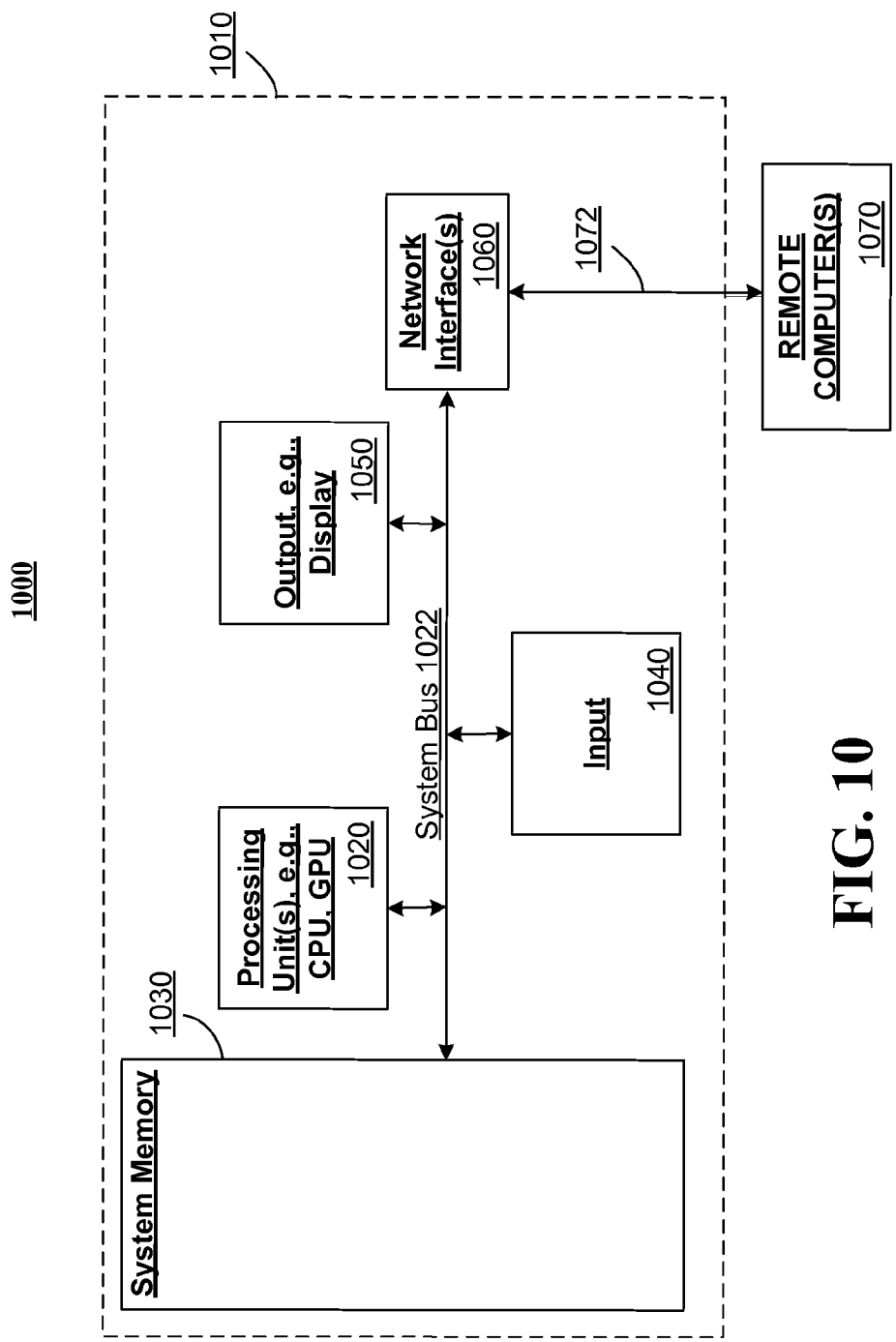
FIG. 10 is an illustration of a schematic diagram of an exemplary computing environment with which one or more aspects described herein can be associated.

FIG. 10 illustrates an example of a suitable computing system environment 1000 in which one or aspects of the aspects described in this disclosure can be implemented. Components of computer 1010 can include, but are not limited to, a processing unit 1020, a system memory 1030, and a system bus 1022 that couples various system components including the system memory to the processing unit 1020.

Computer 1010 typically includes a variety of computer readable media and can be any available media that can be accessed by computer 1010. The system memory 1030 can include computer storage media in the form of volatile and/or nonvolatile memory such as read only memory (ROM) and/or random access memory (RAM). By way of example, and not limitation, memory 1030 can also include an operating system, application programs, other program components, and program data.

A user can enter commands and information into the computer 1010 through input devices 1040 (e.g., keyboard, keypad, a pointing device, a mouse, stylus, touchpad, touch screen, motion detector, camera, microphone or any other device that allows the user to interact with the computer 1010). A monitor or other type of display device can be also connected to the system bus 1022 via an interface, such as output interface 1050. In addition to a monitor, computers can also include other peripheral output devices such as speakers and a printer, which can be connected through output interface 1050.

The computer 1010 can operate in a networked or distributed environment using logical connections to one or more other remote computers, such as remote computer 1080. The remote computer 1080 can be a personal computer, a server, a router, a network PC, a peer device or other common network node, or any other remote media consumption or transmission device, and can include any or all of the elements described above relative to the computer 1010. The logical connections depicted in FIG. 10 include a network 1082, such local area network (LAN) or a wide area network (WAN), but can also include other networks/buses e.g., cellular networks.

Computing devices typically include a variety of media, which can include computer-readable storage media and/or communications media, in which these two terms are used herein differently from one another as follows. Computer-readable storage media can be any available storage media that can be accessed by the computer, can be typically of a non-transitory nature, and can include both volatile and non-volatile media, removable and non-removable media. By way of example, and not limitation, computer-readable storage media can be implemented in connection with any method or technology for storage of information such as computer-readable instructions, program components, structured data, or unstructured data. Computer-readable storage media can include, but are not limited to, RAM, ROM, electrically erasable programmable read only memory (EEPROM), flash memory or other memory technology, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium. In various aspects, the computer-readable storage media can be, or be included within, the memory, contact lens (or components thereof) or reader described herein.

On the other hand, communications media typically embody computer-readable instructions, data structures, program components or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals.

It is to be understood that the aspects described in this disclosure can be implemented in hardware, software, firmware, middleware, microcode, or any combination thereof. For a hardware aspect, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors and/or other electronic units designed to perform the functions described in this disclosure, or a combination thereof.

For a software aspect, the techniques described in this disclosure can be implemented with components or components (e.g., procedures, functions, and so on) that perform the functions described in this disclosure. The software codes can be stored in memory units and executed by processors.

What has been described above includes examples of one or more aspects. It is, of course, not possible to describe every conceivable combination of components or methodologies for purposes of describing the aforementioned aspects, but one of ordinary skill in the art can recognize that many further combinations and permutations of various aspects are possible. Accordingly, the described aspects are intended to embrace all such alterations, modifications and variations that fall within the spirit and scope of the appended claims.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

The aforementioned systems have been described with respect to interaction between several components. It can be appreciated that such systems and components can include those components or specified sub-components. Sub-components can also be implemented as components communicatively coupled to other components rather than included within parent components (hierarchical). Additionally, it is to be noted that one or more components can be combined into a single component providing aggregate functionality. Any components described in this disclosure can also interact with one or more other components not specifically described in this disclosure but generally known by those of skill in the art.

In view of the exemplary systems described above methodologies that can be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks can occur in different orders and/or concurrently with other blocks from what is depicted and described in this disclosure. Where non-sequential, or branched, flow is illustrated via flowchart, it can be appreciated that various other branches, flow paths, and orders of the blocks, can be implemented which achieve the same or a similar result. Moreover, not all illustrated blocks may be required to implement the methodologies described in this disclosure after.

In addition to the various aspects described in this disclosure, it is to be understood that other similar aspects can be used or modifications and additions can be made to the described aspect(s) for performing the same or equivalent function of the corresponding aspect(s) without deviating there from. Still further, multiple processing chips or multiple devices can share the performance of one or more functions described in this disclosure, and similarly, storage can be provided across a plurality of devices. The invention is not to be limited to any single aspect, but rather can be construed in breadth, spirit and scope in accordance with the appended claims.

What is claimed is:

1. A contact lens, comprising:
   a substrate;
   a power component, disposed on or within the substrate, configured to output power;
   a potentiostat, disposed on or within the substrate, and configured to be powered by the power component;
   a sensor, disposed on or within the substrate, electrically coupled to the potentiostat, and configured to sense a level of an analyte in an eye over which the contact lens is configured to be worn, wherein the sensor comprises a working electrode having a plurality of sub-electrodes, and wherein a sensitivity of the sensor is adjustable; and
   an adjustment circuit, disposed on or within the substrate, electrically coupled to the sensor, and configured to control the sensitivity of the sensor by turning one or more of the plurality of sub-electrodes on or off to the potentiostat.

2. The contact lens of claim 1, wherein the adjustment circuit is further configured to control the sensitivity of the sensor by initiation of calibration of the sensor prior to operation of the contact lens.

3. The contact lens of claim 1, wherein the adjustment circuit is further configured to dynamically control the sensitivity of the sensor based, at least, on feedback associated with a level of current output from the sensor.

4. The contact lens of claim 1, wherein the adjustment circuit is further configured to dynamically control the sensitivity of the sensor based, at least, on feedback associated with the level of the analyte being sensed by the sensor.

5. The contact lens of claim 1, wherein the contact lens further comprises a measurement circuit configured to measure a current signal from one or more of the plurality of sub-electrodes switched on to the potentiostat.

6. A contact lens, comprising:
   an adjustment circuit configured to adjust a level of sensitivity of a sensor of the contact lens; and
   a measurement circuit configured to:
      determine a current output from the sensor, wherein the sensor comprises a plurality of sub-electrodes of a working electrode;
      determine whether the current meets a predefined condition for adjustment of a number of the plurality of sub-electrodes, wherein adjustment comprises activation or de-activation of at least one of the plurality of sub-electrodes; and
      output a feedback signal to the adjustment circuit in response to the predefined condition being met, wherein the feedback signal includes at least one of information indicative of a level associated with the current output from the sensor or information indicative of an adjustment to be performed by the adjustment circuit.

7. The contact lens of claim 6, wherein the information indicative of the adjustment to be performed by the adjustment circuit comprises a number of the plurality of sub-electrodes to activate or de-activate.

8. The contact lens of claim 6, wherein the predefined condition comprises the current being within a predefined range of values less than a maximum output current for which the measurement circuit is configured to perform measurement or the current being within a predefined range of values greater than a minimum output current for which the measurement circuit is configured to perform measurement.

9. The contact lens of claim 6, further comprising:
   adjusting a number of activated sub-electrodes prior to at least one of: receipt, by the measurement circuit, of a maximum output current for which the measurement circuit is configured to perform measurement or receipt, by the measurement circuit, of a minimum output current for which the measurement circuit is configured to perform measurement.

10. The contact lens of claim 6, further comprising:
- transmitting to a reader external to the contact lens, the current output from the sensor; and
- receiving, from the reader, at least one of: information indicative of whether the predefined condition has been met or the information indicative of the adjustment to be performed by the adjustment circuit.

11. The contact lens of claim 6, further comprising the sensor.

12. The contact lens of claim 6, wherein the adjustment circuit comprises a plurality of switches coupleable to the plurality of sub-electrodes and configured to activate or de-activate one or more of the plurality of sub-electrodes.

13. An electrode system, comprising:
- a counter electrode of an electrochemical sensor of a contact lens; and
- a working electrode of the electrochemical sensor of the contact lens, the working electrode comprising a plurality of sub-electrodes configured to be turned on or off, wherein the electrode system is further configured to increase sensing sensitivity with an increase in a number of the plurality of sub-electrodes turned on and decrease sensing sensitivity with a decrease in a number of the plurality of sub-electrodes turned off.

* * * * *